(12) United States Patent
Howard et al.

(10) Patent No.: US 10,805,988 B2
(45) Date of Patent: Oct. 13, 2020

(54) METALIZED FABRIC HEATING BLANKET AND METHOD OF MANUFACTURING SUCH

(71) Applicant: Encompass Group, LLC, McDonough, GA (US)

(72) Inventors: Eric James Howard, Dallas, TX (US); Kelley Terrell, Ferris, TX (US); Mark Beran, Neenah, WI (US)

(73) Assignee: Encompass Group, LLC, McDonough, GA (US)

( * ) Notice: Subject to any disclaimer, the term of this patent is extended or adjusted under 35 U.S.C. 154(b) by 325 days.

(21) Appl. No.: 15/841,044

(22) Filed: Dec. 13, 2017

(65) Prior Publication Data

US 2018/0270907 A1    Sep. 20, 2018

Related U.S. Application Data

(60) Provisional application No. 62/471,103, filed on Mar. 14, 2017.

(51) Int. Cl.
  *H05B 3/34*    (2006.01)
  *H05B 3/14*    (2006.01)
  *A61F 7/00*    (2006.01)

(52) U.S. Cl.
  CPC ............ *H05B 3/342* (2013.01); *A61F 7/0097* (2013.01); *H05B 3/145* (2013.01); *H05B 2203/002* (2013.01); *H05B 2203/011* (2013.01); *H05B 2203/016* (2013.01); *H05B 2203/017* (2013.01); *H05B 2203/034* (2013.01); *H05B 2203/036* (2013.01)

(58) Field of Classification Search
  CPC .. H05B 3/342; H05B 3/145; H05B 2203/036; H05B 2203/017; H05B 2203/011; H05B 2203/002; H05B 2203/034; H05B 2203/016; H05B 3/36; A61F 7/0097; A61F 7/007; A61F 7/08; A61F 2007/0071; A61F 2007/0086; A47C 21/048
  See application file for complete search history.

(56) References Cited

U.S. PATENT DOCUMENTS

| | | |
|---|---|---|
| 6,653,607 B2 | 11/2003 | Ellis et al. |
| 6,924,467 B2 | 8/2005 | Ellis et al. |
| 6,933,469 B2 | 8/2005 | Ellis et al. |
| 6,967,309 B2 | 11/2005 | Wyatt et al. |
| 7,176,419 B2 | 2/2007 | Ellis et al. |
| 7,196,289 B2 | 3/2007 | Ellis et al. |
| 7,786,408 B2 | 8/2010 | Augustine et al. |
| 7,851,729 B2 | 12/2010 | Augustine et al. |

(Continued)

*Primary Examiner* — Patrick M. Buechner
(74) *Attorney, Agent, or Firm* — Baker Donelson

(57) ABSTRACT

A warming blanket (8) has a metalized fabric exterior layer and a heating element formed from a random fiber carbon veil material (52). A conductive ink layer (56) is deposited onto opposite side edges of the carbon veil material as side rails. Lower conductive strips (58) are attached onto a bottom edge of the carbon veil material. Each lower conductive strip is electrically coupled to a side rail. The lower conductive strips have connecting ends (60) which are spaced from each other so as to accept a connection circuit board. Side conductive strips (62) are coupled to the conductive ink side rails. Electrical current controlled by the connection circuit board is passed through the carbon veil material to create heat.

16 Claims, 8 Drawing Sheets

(56) References Cited

U.S. PATENT DOCUMENTS

| | | | |
|---|---|---|---|
| 8,062,343 B2 | 11/2011 | Augustine et al. | |
| 8,283,602 B2 | 10/2012 | Augustine et al. | |
| 8,624,164 B2 | 1/2014 | Deibel et al. | |
| 8,772,676 B2 | 7/2014 | Augustine et al. | |
| 9,687,093 B2 | 6/2017 | Giles et al. | |
| 2002/0153368 A1* | 10/2002 | Gardner | B29C 70/82 |
| | | | 219/545 |
| 2007/0068923 A1* | 3/2007 | Augustine | A61F 7/007 |
| | | | 219/465.1 |
| 2008/0093356 A1* | 4/2008 | Pizzi | H05B 3/34 |
| | | | 219/474 |
| 2010/0161016 A1* | 6/2010 | Augustine | A61F 7/0097 |
| | | | 607/112 |
| 2010/0200558 A1* | 8/2010 | Liu | H05B 3/342 |
| | | | 219/212 |
| 2010/0217260 A1* | 8/2010 | Aramayo | A61B 18/16 |
| | | | 606/41 |
| 2010/0255277 A1 | 10/2010 | Platt et al. | |
| 2011/0233193 A1* | 9/2011 | Cheng | H05B 3/36 |
| | | | 219/549 |
| 2014/0263265 A1 | 9/2014 | Augustine et al. | |
| 2014/0316494 A1 | 10/2014 | Augustine et al. | |
| 2015/0072113 A1* | 3/2015 | Terrell | B32B 5/022 |
| | | | 428/196 |
| 2015/0148874 A1 | 5/2015 | Augustine et al. | |
| 2015/0327332 A1 | 11/2015 | Augustine et al. | |
| 2016/0143091 A1* | 5/2016 | Augustine | H05B 3/36 |
| | | | 219/528 |
| 2017/0135855 A1* | 5/2017 | Stefan | A61F 7/007 |
| 2018/0124871 A1* | 5/2018 | Barfuss | B32B 7/12 |
| 2018/0279416 A1* | 9/2018 | Sajic | H05B 1/0238 |
| 2019/0240066 A1* | 8/2019 | Hood | A61F 7/0097 |
| 2019/0351153 A1* | 11/2019 | Howard | A61M 5/445 |

\* cited by examiner

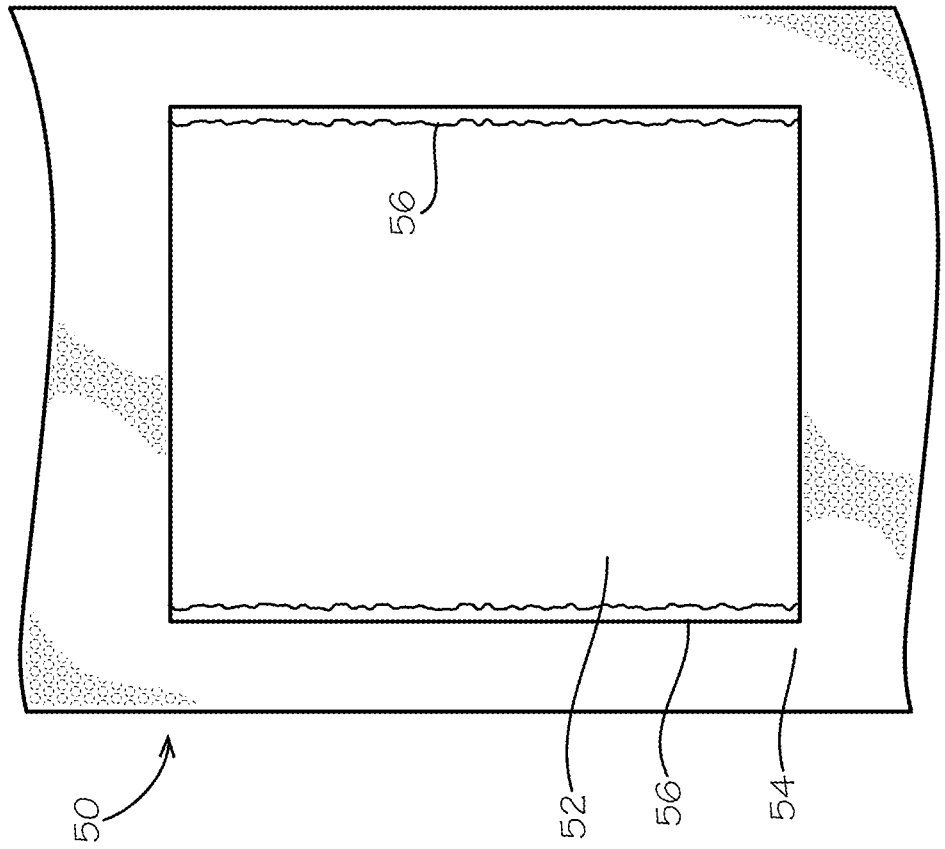
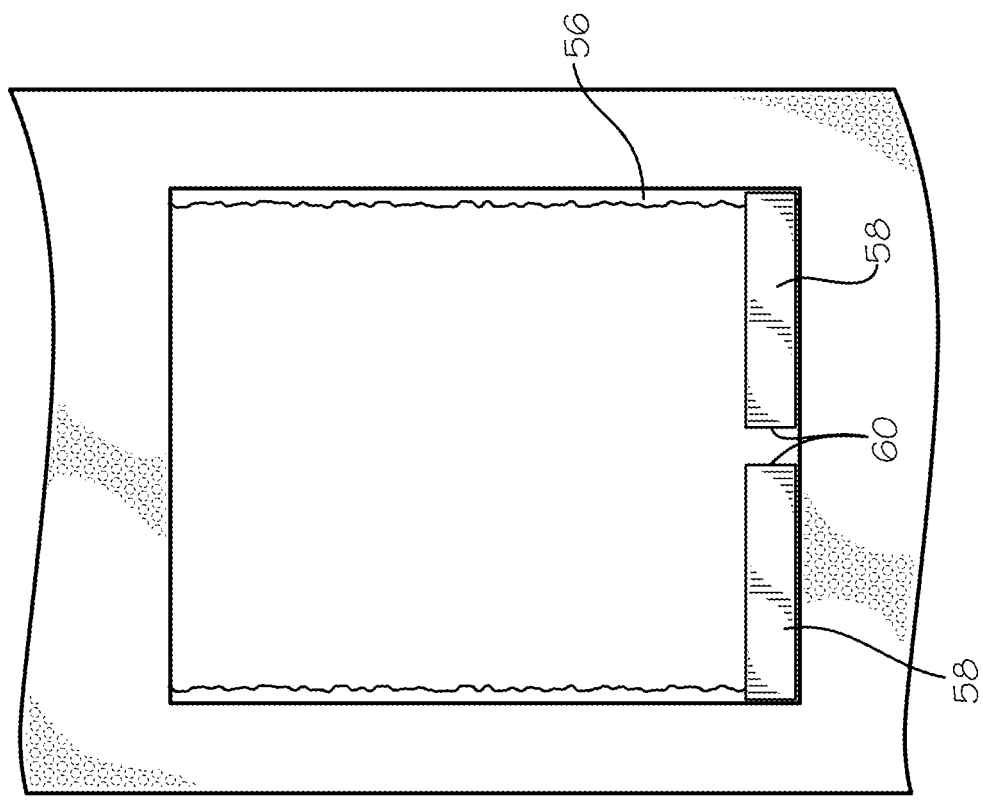
FIG. 7
FIG. 8

METALIZED FABRIC HEATING BLANKET AND METHOD OF MANUFACTURING SUCH

REFERENCE TO RELATED APPLICATION

Applicant claims the benefit of U.S. Provisional Patent Application Ser. No. 62/471,103 filed Mar. 14, 2017 and entitled Metalized Fabric Heating Blanket.

TECHNICAL FIELD

This invention relates generally to heating blankets, and more particularly to heating blankets utilizing metalized fabrics and the method of manufacturing such and a method of manufacturing such.

BACKGROUND OF THE INVENTION

Insulative blankets and the like have been made for centuries. Such blankets have traditionally been made of a wool or cotton cloth. These materials have provided a certain amount of heat retaining qualities, however, they are not optimal for such a task.

It has recently been discovered that blankets and clothing may be made of a metalized material to provide the added benefit of infrared heat reflecting capabilities to better prevent heat loss from a person. These products may be used as outdoor blankets, medical patient coverings, or other clothing wherein the conservation of body heat is desired. These metalized fabrics however are usually stiff and not soft to the touch.

Encompass Group, LLC has provided a metalized fabric material under the tradename Thermoflect for many years. This metalized fabric has four discrete layers which are bonded together to form the fabric. These four layers include a clear polyethylene layer, a vaporized aluminum layer, a second polyethylene layer, and a smooth surface spunbond polypropylene layer, these layers being recited in sequence from an exterior surface to an interior surface facing a person donning an article incorporating the fabric. It would be desirous to have a metalized fabric material which is softer to the touch and less stiff to provide better draping and loft characteristics. It would also be desirous to provide supplemental heating to warm the person in a quicker and more efficient manner.

It would be beneficial to provide a warming blanket with metalized material which is able to provide an efficient, fast, and consistent heat to a person so that it may be more suitable for use upon a person than those of the prior art. Accordingly, it is to the provision of such that the present invention is primarily directed.

SUMMARY OF THE INVENTION

In a preferred form of the invention a heating blanket comprises a carbon veil material, a first electrically conductive strip electrically coupled along a first side of the carbon veil, a second electrically conductive strip electrically coupled along a second side of the carbon veil material opposite the first side of the carbon veil material, a first electrically insulative layer overlaying a first surface of the carbon veil material, a second electrically insulative layer overlaying a second surface of the carbon veil material oppositely disposed from the first surface of the carbon veil material, and an electrical control circuit electrically coupled to the first electrically conductive strip and the second electrically conductive strip. With this construction, current passing from the electrical control circuit to the first and second electrically conductive strips passes through the carbon veil to create heat.

BRIEF DESCRIPTION OF THE DRAWINGS

FIGS. 7-12 are a series of top view of a warming blanket in another preferred embodiment, showing the manufacturing process.

DETAILED DESCRIPTION

Figure 1:
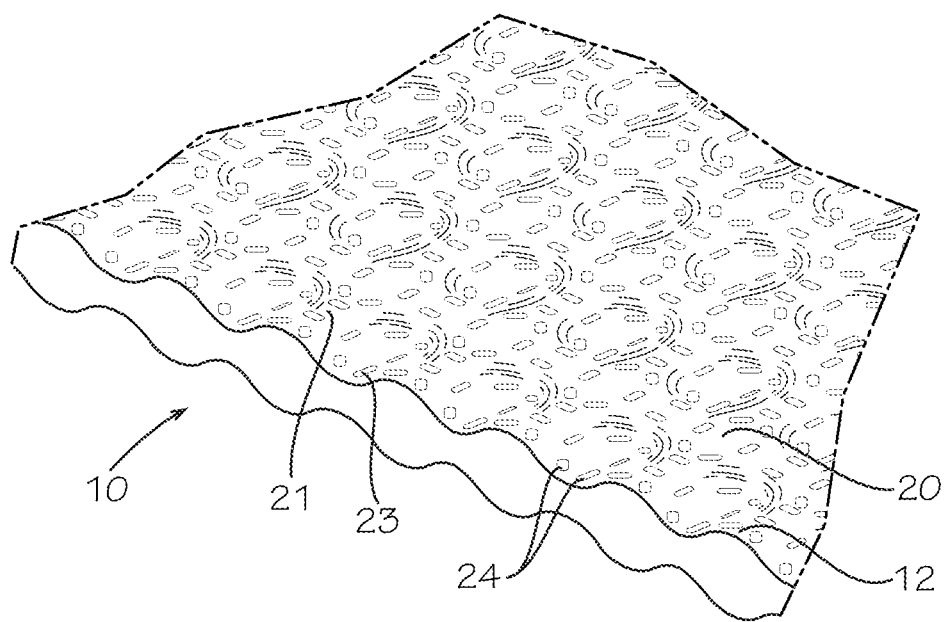
FIG. 1 is a perspective view of a warming blanket embodying principles of the invention in a preferred form.
Figure 2:
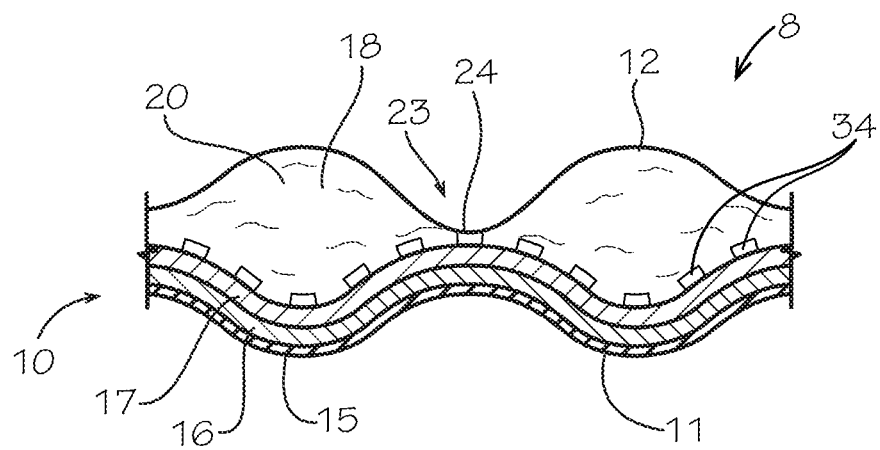
FIG. 2 is a cross-sectional view of a portion of the warming blanket of FIG. 1.
Figure 3:
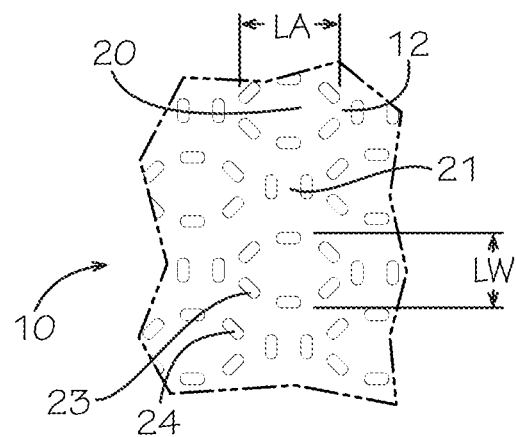
FIG. 3 is a top view of a portion of the warming blanket of FIG. 1.

With reference next to the drawings, there is shown a warming blanket 8 made in part with a metalized fabric 10 embodying principles of the invention in a preferred form. The warming blanket 8 has a lower surface 11 which is intended to face away from a person (patient) overlaid with or donning the material and an upper surface 12 which is intended to face the person (patient). The metalized fabric includes a first layer 15 of clear thermoplastic (for example a polyethylene) material, a second layer 16 of vaporized aluminum material (metalized layer), a third layer 17 of thermoplastic (for example a polyethylene) material, and a fourth layer 18 of lofted billow spunbond thermoplastic (for example a polypropylene)non-woven material. The exterior surface of the first layer 15 constitutes the fabric lower surface 11, while the exterior surface of the fourth layer 18 constitutes the upper surface 12.

The warming blanket 8 also includes a resistive heating portion 30 positioned between the third layer 17 and the fourth layer 18. The resistive heating portion 30 is positioned distally from the perimeter or outer edge of the warming blanket 31 and metalized fabric 10 so that a surrounding margin 32 is formed therebetween.

Figure 4:
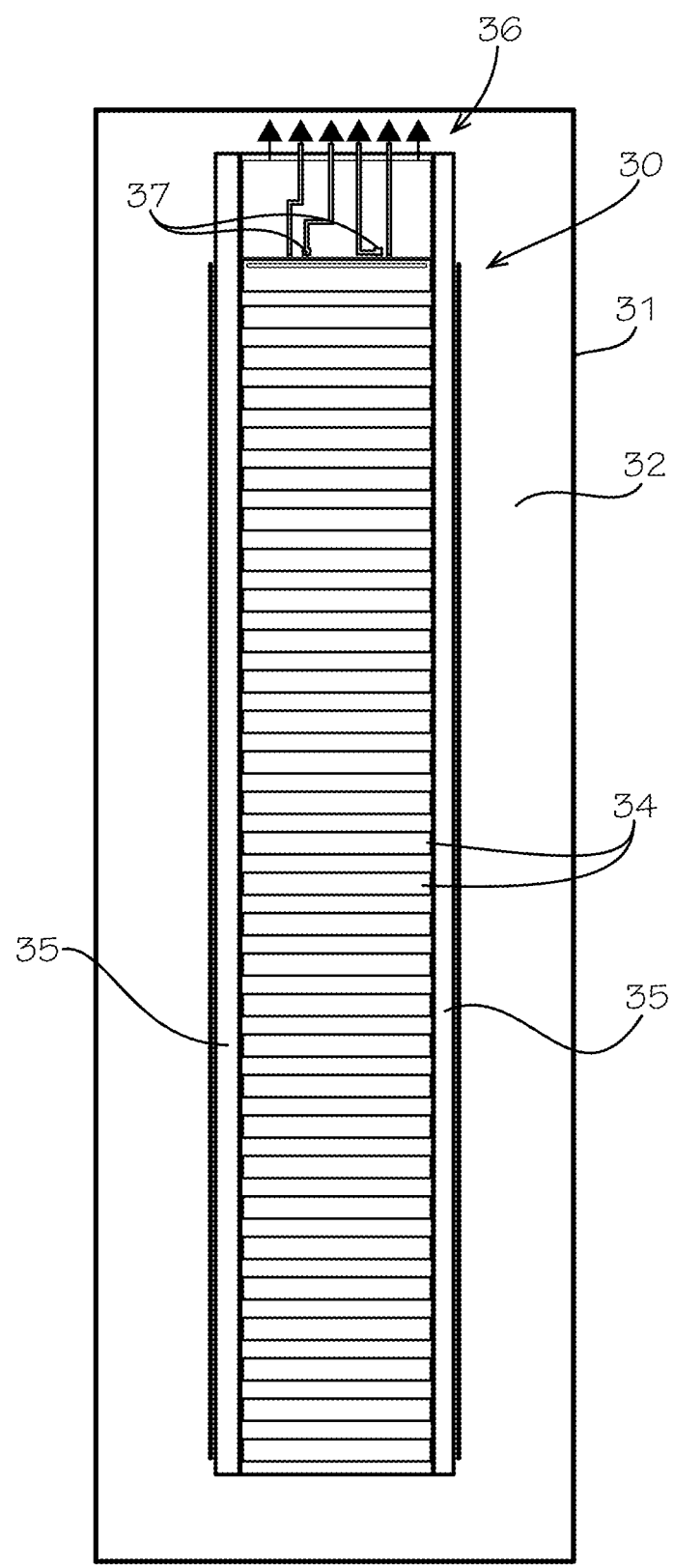
FIG. 4 is a plan view of the warming blanket of FIG. 1.

The resistive heating portion 30 has heater trace resistors or heating elements 34 arranged in a longitudinal array with each heating element 34 extending laterally, as best shown in FIG. 4. The heating elements 34 are formed by depositing a conventional electrically conductive ink upon the third layer 17 in the desired pattern. The heating elements 34 are electrically joined together through a pair of conductive tapes 35 coupled to the ends of the heating elements. The conductive tapes 35 may be made of a metal, such as copper, or in the alternative, the conductive tapes 35 may be replaced by additional conductive ink strips or any other configuration of a conductive element. The resistive heating portion 30 may also include a convention flat flex crimp pin type connectivity or coupler 36 to allow a quick connect to a controller, which may also include thermistors 37, or thermocouples, to regulate the current and temperature of the warming blanket 8.

The warming blanket 8 may have an input voltage of 100 to 250 VAC and a maximum blanket power of 7 W @12 VDC to 109 W @48 VDC.

The metalized fabric is manufactured by joining the third layer 17 of thermoplastic material having the resistive heating portion 30 thereon to the fourth layer 18 of spunbond thermoplastic non-woven material. The second layer 16 of vaporized aluminum material is then deposited or joined onto the third layer 17 via a vacuum deposit chamber. The first layer 15 is then extruded or joined onto the second layer 16. The combination of layers is then passed through cold calender rollers which seals the layers together in a pattern that forms a series, matrix or field of large pillowed areas or regions 20 surrounded at four sides by smaller pillowed regions 21. The large pillowed region 20 is generally oval in shape with a longitudinal length LA of approximately $3/16$ of an inch and a lateral width LW of approximately $2/16$ of an inch. The seals 23 themselves are non-continuous or fragmented, as they are formed by several unjoined segments 24 which also helps in providing a less stiff feel to the metalized fabric by breaking up the seals which tend to be stiffer than those areas of the fabric which are not sealed, i.e., the bonding of the material at the seals tends to stiffen the sealed areas and thereby tends to stiffen the overall material decreasing its drapability and loft. The metalized fabric of the present invention is fused, bonded or sealed on approximately 14% of the material, as opposed to the prior art material which included at a minimum 18% fusing, bonding or sealing.

It is believed that the position of the heating elements between the person and the metalized second layer 16 provides for an more even distribution of heat. Heat produced from the heating elements is reflected by the metalized second layer 16 back onto the person. Thus, heat initially drawn away from the person is not lost to ambient environment and is instead used to heat the person, a distinct advantage over the prior art.

It is believed that the pillowing of the metalized fabric provides for greater insulative qualities, a softer feel, better glare reduction, improved drapability, and improved loft.

Another discovered advantage has been the materials improved cross-direction tearing resistance. A test was conducted comparing the prior Thermoflect metalized material, previously described, to the metalized fabric of the present invention. The metalized fabric of the present invention was found to have a cross directional tearing factor of 435.7, while the prior Thermoflect metalized material had a tested cross directional tearing factor of 393. This test shows an improvement in tearing resistance of approximately eleven percent (11%).

Figure 5:
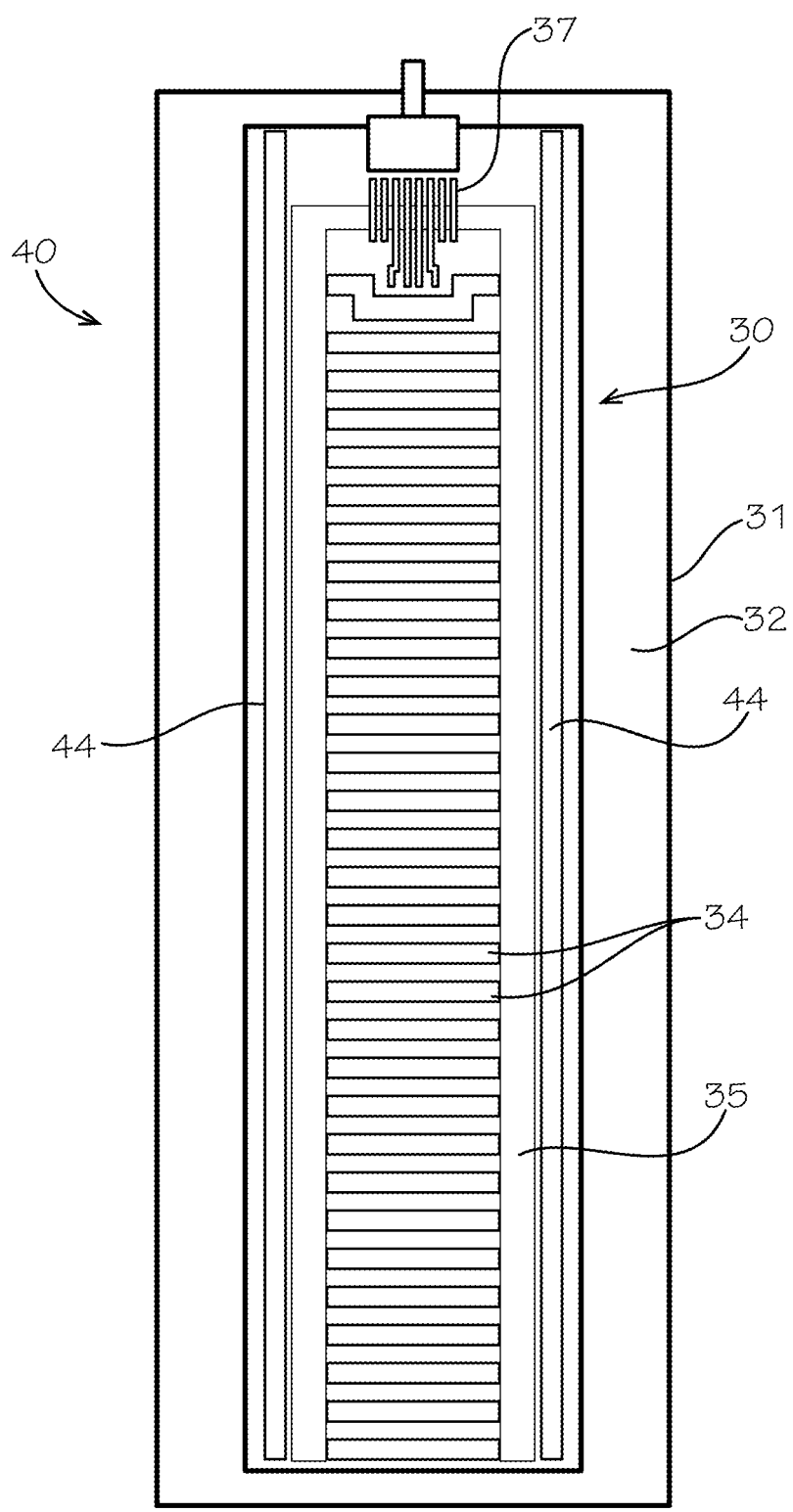
FIG. 5 is a plan view of a warming blanket embodying principles of the invention in another preferred form.
Figure 6:
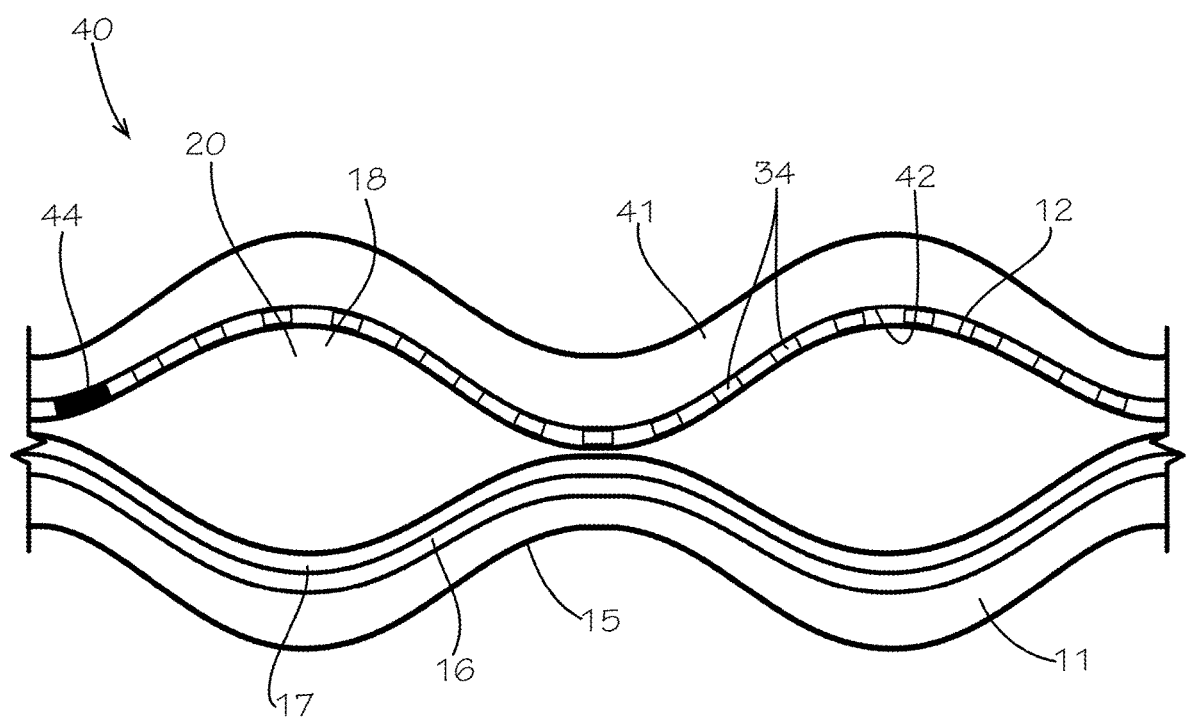
FIG. 6 is a cross-sectional view of a portion of the warming blanket of FIG. 5.

As an alternative to the first embodiment, a second embodiment of the invention in a preferred form is shown in FIGS. 5 and 6. Here, warming blanket 40 has the previously described first layer 15, second layer 16, third layer 17 and fourth layer 18 are formed as a unitary structure. A fifth layer 41 is coupled to the fourth layer 18. The fifth layer 41 may be a spunbond thermoplastic (for example a polypropylene) non-woven material. The fifth layer 41 includes the resistive heating portion 30, and especially all the previously described components including the heating elements 34 which may be in the form of electrically conductive ink, bonded or coupled to the interior surface 42 of the fifth layer 41 facing the fourth layer 18.

A pair of double-sided tape strips 44 may be applied to the fifth layer 41 so that it may be attached or coupled to a pre-existing warming blanket. Also, if need be, the fifth layer 41 with the electronic components may be easily removed or released from the warming blanket. As such, an existing warming blanket may be converted from a static or strictly body heat capturing warming blanket to a positive or active electrically resistive heat added warming blanket. The warming blanket may then be reconfigured to a static body heat capturing warming blanket by removing the fifth layer 42 and electronic components. In this manner, the electronic components may be attached and then removed from multiple warming blankets should they become soiled or otherwise unusable and may be disposed. This disposability decreases the expense involved in providing warming blankets having resistive heating capabilities.

It is believed that this embodiment provides an even higher amount of heat dispersement or distribution as a portion of the heat from the heating elements 34 initially radiating in the direction away from the patient is dispersed as it passes through the fourth layer 18, is reflected by the second layer 16, and then disperses even more as it passes again through the fourth layer 18 prior to reaching the person, i.e., the heat passes through the fourth layer 18 twice before reaching the person. This also allows the temperature of the conductive heating element 34 to be set at a lower temperature because of the additional reflected heat being directed back to the person.

It should be understood that as used herein the term "lofted" is intended to mean something that is fluffed, fluffy, expanded, expanded layers, or the like. Also, the term "billow" or "billowed" is intended to mean raised, embossed, undulating surface, having lofted areas, or the like. The use of a lofted inner material is believed to allow the heat from the heating elements 34 and that reflected back from the metalized second layer 16 to spread so as to provide a more even heating, as opposed to a concentration of the heat should a thin layer be utilized.

With reference next to the embodiment of FIGS. 7-13, there is shown a heating blanket 40 in another preferred form of the invention.

Here, the heating elements 34 are formed by adhering a small patch 53 of electrically insulative spunbond material to an exterior facing surface of a carbon veil material 52, wherein the carbon veil material 52 may be a sheet or matt of randomly orientated carbon fibers. The carbon veil material 52 is then adhered, through sewing, adhesive, sonic welding or the like, to a second layer of electrically insulative spunbond material 63 which will be later bonded to a previously discussed metalized fabric 54. The metalized fabric 54 is generally the same as that previously described and which includes the first layer 15 of clear thermoplastic (for example a polyethylene) material, the second layer 16 of vaporized aluminum material (metalized layer), a third layer 17 of thermoplastic (for example a polyethylene) material, and a fourth layer 18 of lofted billow spunbond thermoplastic (for example a polypropylene)non-woven material. The third layer 17 and fourth layer 18 may also be electrically insulative.

Next, a conductive strip in the form of a conductive ink layer 56, which may be made of nickel or silver ink, is deposited, sprayed upon, or printed onto opposite side edges of the carbon veil material 52 as thin strips or side rails 56, also shown in FIG. 7. The conductive ink side rails 56 acts to locally connect the random conductive fibers at different depth of the carbon veil material 52.

With reference next to FIG. 8, lower conductive strips 58 are then sewed on, or alternatively attached by electrically conductive adhesive or other bonding method, onto a bottom edge of the carbon veil material 52. Each lower conductive strip 58 is electrically coupled to a side rail 56. The lower conductive strips 58 may be made of an aluminum foil or other electrically conductive material. The lower conductive strips 58 are electrically insulated from the carbon veil material 52. The lower conductive strips 58 have connecting ends 60 which are spaced from each other so as to accept a connection circuit board described in more detail hereinafter.

Figure 9:
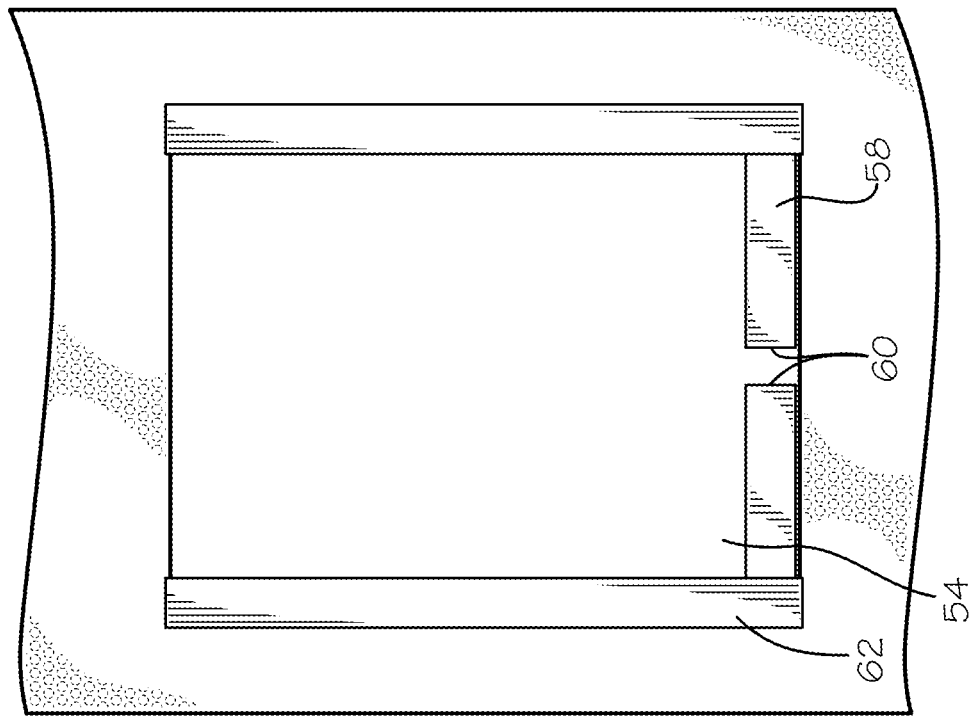

With reference next to FIG. 9, side conductive strips 62 are then sewed onto the conductive ink side rails 56 in electrical contact with the conductive ink side rails 56. The nickel boundary of the conductive ink side rails 56 prevent resistance drift from occurring. The side conductive strips 62 are also sewn so as to be in electrical contact with the lower conductive strips 58.

The second layer of spunbond material 63 is then laminated or otherwise bonded (adhesive, sonic welding, or the like) about the periphery of the fourth layer (spunbond material) 18 and/or carbon veil material 52, thereby sandwiching the carbon veil material 52 between two layers of spunbond material. The second layer of spunbond material 63 protects the carbon veil material 52 while providing a soft exterior layer for patient comfort and safety. The combination of the second layer of spunbond material 63 with the first layer of spunbond material (metalized fabric) essentially creates an envelope surrounding or encasing the carbon veil.

Figure 10:
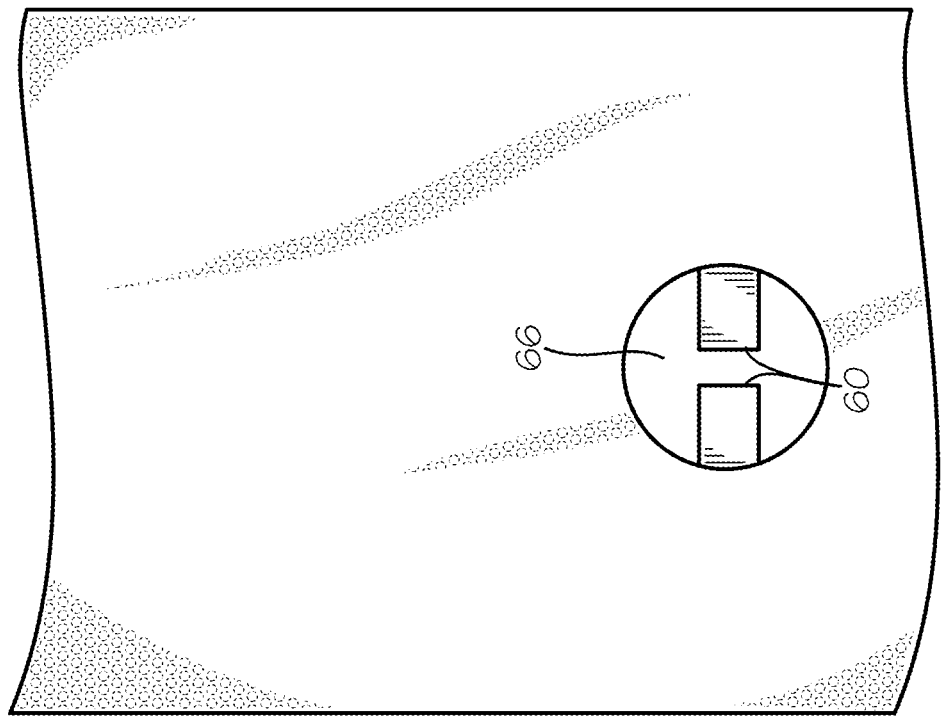
Figure 12:
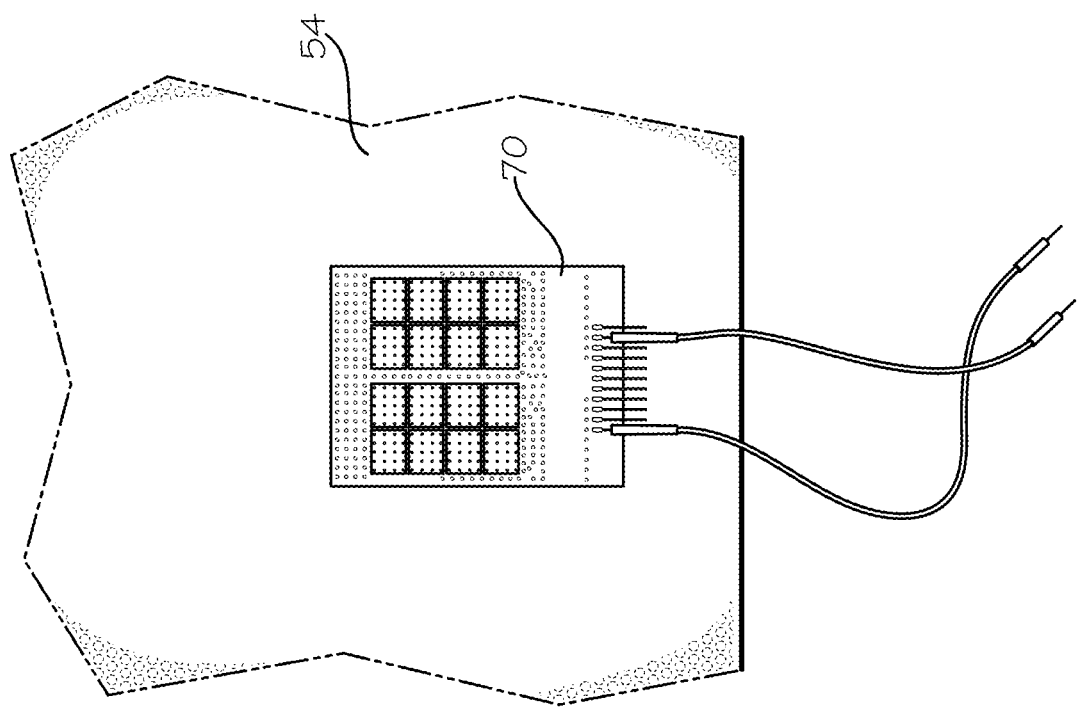
Figure 11:
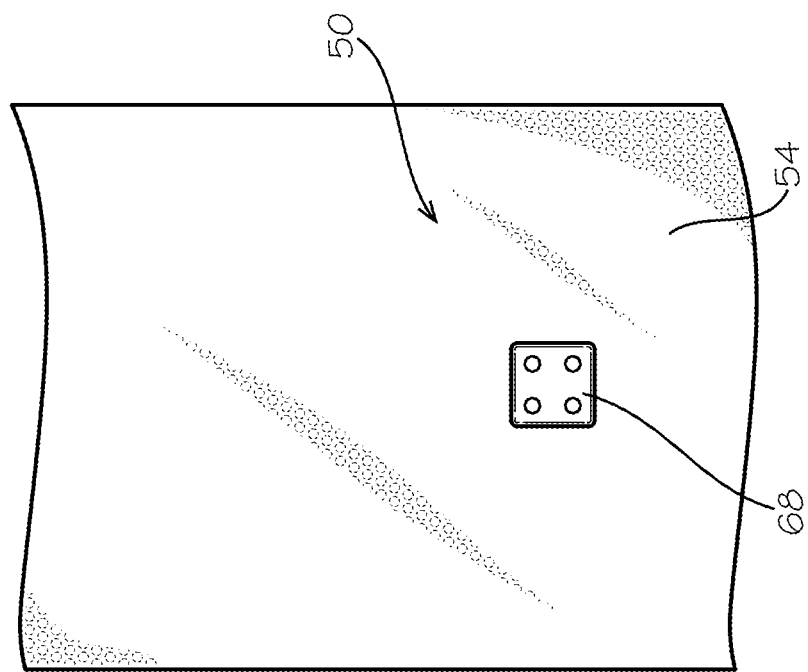
Figure 13:
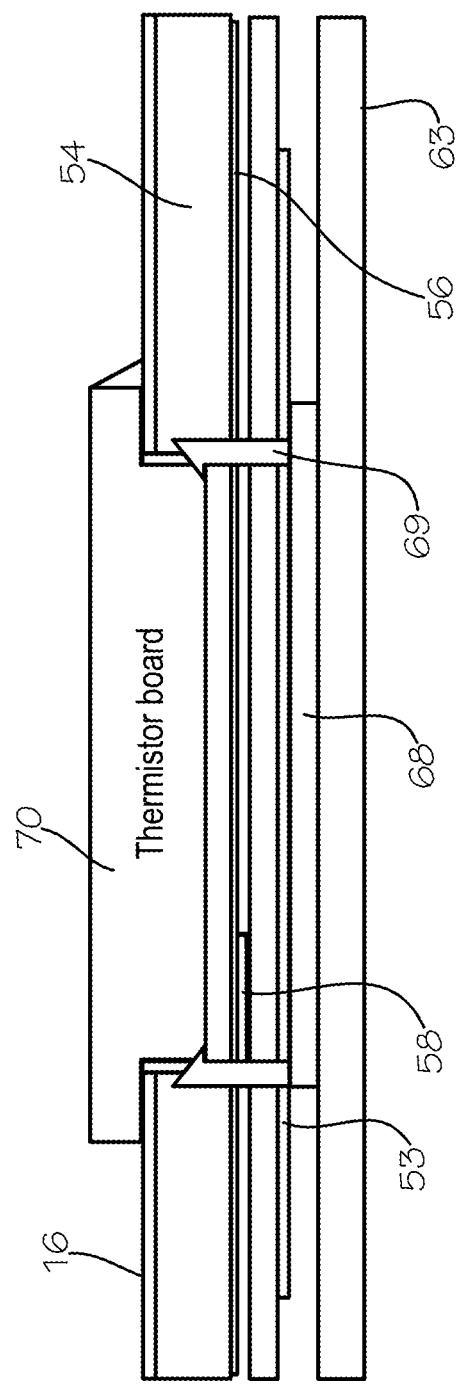
FIG. 13 is a cross-sectional view of a portion of the warming blanket shown in FIGS. 7-12.

With reference next to FIG. 10, a hole or opening 66 is cut into the metalized fabric 54 so as to expose the connecting ends 60 of the lower conductive strips 58. A backing plate 68 is then attached to the backside of the second layer of spunbond material 63 at the position of the opening 66, as shown in FIG. 11, or to a patch of spun bond material which is then adhered to the patient side of the blanket. The backing plate 68 may be passed through a slot or cut 67 in the second layer of spunbond material 63 so as to be placed flush against the patch 53, as shown in FIG. 13. The use of the backing plate 68 provides local support of the connection points of the warming blanket as well as providing pressure between the contact surfaces of the thermistor board and the lower conductive strips 58 (cross rails). The backing plate 68 includes a set of mounting prongs 69 which extend through or are punched through the patent 53 and carbon veil material 52 so that they may engage, fit upon a snap-on circuit board 70 containing thermistors (thermistor plate 71), or thermocouples. The circuit board 70 is then mounted to the exterior surface of the metalized fabric 54 and connected to the connecting ends 60 of the lower conductive strips 58, as shown in FIGS. 12 and 13. The circuit board 70 includes a large array of vias to assist heat transfer to the where the thermistors are located. The use of a large circuit board for connection purposes provides a more accurate average temperature of the heating fabric (carbon veil material), i.e., the temperature is sensed over a larger area for averaging purposes to minimize the possibility of errors. The vias transfer heat to the top side of the circuit board so that the thermistors can be captured within the connector housing. This also shields the thermistors for the safety of the operator.

In use, electric current is controlled through the circuit board 70 and passed to the connecting ends 60 of the lower conductive strips 58. The current then travels to the side conductive strips 62 and conductive ink side rails 56 where it is then passed to the carbon veil material 52 wherein resistive heat is created. The metalized fabric reflects the heat to produce an even distribution and more efficient use of the heat.

The circuit board 70 uses multiple thermistors to minimize variance. The placement of the thermistors on the circuit board 70 enables them to be on a re-useable portion of the warming blanket 50 rather than the disposable "blanket" or material covering portion. This placement reduces the replacement costs of the warming blanket.

It is believed that the sewing of the conductive foil of the lower conductive strips 58 and side conductive strips 62 to the second layer of spunbond material 63 and carbon veil material 52 provides a better electrical connection. It is also believed that the sewing maintains a better drapeability of the warming blanket. The improved drapeability is important for patient comfort, effective warming, and reduced cost of manufacture.

The sewing process of the lower conductive strips 58 and the side conductive strips 62 preferably is accomplished with the use of non-conductive cotton-poly blend threads.

It should be understood that the description is for one method of constructing the warming blanket. The exact sequence of the steps involved in the construction may differ while still embodying the invention.

It should be understood that sewing, adhesive bonding, sonic welding, heat welding, or any other conventional method of bonding or coupling, as used herein, are equivalent.

It thus is seen that a heating blanket using a metalized fabric and a method of manufacturing such is now provided which overcomes problems associated with heating blankets of the prior art. It should of course be understood that many modifications may be made to the specific preferred embodiment described herein, in addition to those specifically recited herein, without departure from the spirit and scope of the invention as set forth in the following claims.

The invention claimed is:

1. A heating blanket comprising, a carbon veil material;
a first electrically conductive rail electrically coupled along a first side of said carbon veil;
a second electrically conductive rail electrically coupled along a second side of said carbon veil material opposite said first side of said carbon veil material;
a first electrically insulative layer overlaying a first surface of said carbon veil material;
a second electrically insulative layer overlaying a second surface of said carbon veil material oppositely disposed from said first surface of said carbon veil material;
an electrical control circuit electrically coupled to said first electrically conductive rail and said second electrically conductive rail;
a first electrically conductive strip overlaying and in electrical contact with said first electrically conductive rail, and
a second electrically conductive strip overlaying and in electrical contact with said second electrically conductive rail,
wherein said first and second electrically conductive rails are made of an electrically conductive ink,
whereby current passing from the electrical control circuit to the first and second electrically conductive rails passes through the carbon veil to create heat.

2. The heating blanket of claim 1 wherein said carbon veil material is a material of randomly orientated carbon fibers.

3. The heating blanket of claim 1 wherein said first and second electrically conductive strips are made of a metallic foil.

4. The heating blanket of claim 1 wherein said first electrically insulative layer includes a metallic layer, a first thermoplastic layer overlaying a first surface of said metallic layer, and a second thermoplastic layer overlaying a second surface of said metallic layer oppositely disposed from said first surface of said metallic layer.

5. The heating blanket of claim 4 wherein said first electrically insulative layer is a spunbond material.

6. The heating blanket of claim 5 wherein said second electrically insulative layer is a spunbond material.

7. A heating blanket comprising,
- an exterior envelope of non-conductive material; an interior layer of carbon fiber material encased within said exterior envelope;
- an electrical control circuit electrically coupled to said interior layer of carbon fiber material;
- a first electrically conductive rail electrically coupled along a first side of said carbon fiber material;
- a second electrically conductive rail electrically coupled along a second side of said carbon fiber material opposite said first side of said carbon fiber material;
- a first electrically conductive strip overlaying and in electrical contact with said first electrically conductive ink rail, and
- a second electrically conductive strip overlaying and in electrical contact with said second electrically conductive ink rail,
- wherein said first electrically conductive rail is an electrically conductive ink rail and wherein said second electrically conductive rail is an electrically conductive ink rail
- whereby current passes from the electrical control circuit to the interior layer of carbon fiber material to create heat.

8. The heating blanket of claim 7 wherein at least a portion of said exterior envelope includes a metallic layer, a first thermoplastic layer overlaying a first surface of said metallic layer, and a second thermoplastic layer overlaying a second surface of said metallic layer oppositely disposed from said first surface of said metallic layer.

9. The heating blanket of claim 7 wherein said interior layer of carbon fiber material is a material of randomly orientated carbon fibers.

10. The heating blanket of claim 7 wherein said exterior envelope is made of a thermoplastic, spunbond material.

11. The heating blanket of claim 7 wherein said first and second electrically conductive strips are made of a metallic foil.

12. A heating blanket comprising,
- a carbon veil material;
- a first rail of electrically conductive ink deposited along a first side of said carbon veil material;
- a second rail of electrically conductive ink deposited along a second side of said carbon veil material opposite said first rail of electrically conductive ink;
- a first covering layer overlaying a first surface of said carbon veil material;
- a first electrically conductive strip overlaying and in electrical contact with said first rail of electrically conductive ink;
- a second electrically conductive strip overlaying and in electrical contact with said second rail of electrically conductive ink;
- a second covering layer overlaying a second surface of said carbon veil material oppositely disposed from said first surface of said carbon veil material, and
- an electrical control circuit electrically coupled to said first and second rails of electrically conductive ink, whereby current passing from the electrical control circuit to the first and second rails of electrically conductive ink passes through the carbon veil to create heat.

13. The heating blanket of claim 12 wherein said carbon veil material is a material of randomly orientated carbon fibers.

14. The heating blanket of claim 12 wherein said first and second electrically conductive strips are made of a metallic foil.

15. The heating blanket of claim 12 wherein said first covering layer includes metallic layer and at least one thermoplastic layer overlaying said metallic layer.

16. The heating blanket of claim 15 wherein said at least one thermoplastic layer is a spunbond material.

* * * * *